(12) United States Patent
Strauss et al.

(10) Patent No.: US 6,448,447 B1
(45) Date of Patent: *Sep. 10, 2002

(54) FLUOROBORATE SALTS COMPRISING A REACTIVE CATION AND USES THEREOF

(75) Inventors: Steven H. Strauss; Sergei V. Ivanov, both of Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/704,270

(22) Filed: Oct. 31, 2000

Related U.S. Application Data

(63) Continuation-in-part of application No. 09/465,563, filed on Dec. 17, 1999, now Pat. No. 6,180,829, which is a continuation of application No. 09/049,420, filed on Mar. 27, 1998, now Pat. No. 6,130,357.

(60) Provisional application No. 60/043,041, filed on Apr. 3, 1997, and provisional application No. 60/058,836, filed on Sep. 11, 1997.

(51) Int. Cl.[7] .................................................. C07F 5/02
(52) U.S. Cl. ..................... 568/3; 568/4; 568/5; 564/10; 564/11; 556/7
(58) Field of Search .................. 564/10, 11; 568/3, 568/4, 5; 423/276, 277, 284; 556/7, 8

(56) References Cited

U.S. PATENT DOCUMENTS

| | | | | |
|---|---|---|---|---|
| 3,196,098 A | * | 7/1965 | Mochel | |
| 3,428,439 A | * | 2/1969 | Hertler et al. | |
| 3,551,120 A | * | 12/1970 | Miller et al. | |
| 3,779,777 A | * | 12/1973 | Bigelow | |
| 6,130,357 A | * | 10/2000 | Strauss et al. | 568/3 |
| 6,180,829 B1 | * | 1/2001 | Strauss et al. | 568/3 |

OTHER PUBLICATIONS

CA:128:257530 abs of J Am Chem Soc by Ivanov et al 120(17) pp 4224–4225 1998.*
CA:124:202361 abs of Chem Ber by Lomme et al 128(12) pp 1225–9 1995.*
CA:129:276014 abs of WO 9843983 Oct. 1998.*

* cited by examiner

Primary Examiner—Jean F. Vollano
(74) Attorney, Agent, or Firm—Townsend and Townsend and Crew LLP

(57) ABSTRACT

The present invention provides weakly coordinating anion salts comprising a reactive cation and uses thereof. In particular, the present invention provides compounds of the formula $M_xQ_y$ and uses thereof. Preferably, each M is independently a cation with at least one M being a reactive cation as defined herein. Q is a fluorinated polyhedral borate moiety. And x and y are absolute values of the oxidation states of Q and M, respectively.

32 Claims, 3 Drawing Sheets

FLUOROBORATE SALTS COMPRISING A REACTIVE CATION AND USES THEREOF

CROSS REFERENCE TO RELATED APPLICATIONS

This application is a continuation-in-part application of U.S. patent application Ser. No. 09/465,563, filed Dec. 17, 1999, now U.S. Pat. No. 6,180,829, issued on Jan. 30, 2001, which is a continuation application of U.S. patent application Ser. No. 09/049,420, filed on Mar. 27, 1998, now U.S. Pat. No. 6,130,357, issued Oct. 10, 2000, which claims priority benefits of U.S. Provisional Patent Application Serial No. 60/043,041, filed Apr. 3, 1997 and No. 60/058,836, filed Sep. 11, 1997, all of which are incorporated herein by reference in their entirety.

FIELD OF THE INVENTION

The present invention relates to weakly coordinating anion salts comprising a reactive cation and uses thereof. In particular, the present invention relates to fluoroborate salts comprising a reactive cation. Specifically, the present invention provides compounds of the formula $M_xQ_y$, where M, Q, x, and y are those defined herein.

BACKGROUND OF THE INVENTION

Weakly coordinating anion salts comprising a reactive cation are useful in variety of reactions including polymerization reactions, coupling reactions, and other chemical reactions which is facilitated by an appropriate cation. Useful reactive cations include silver cation, silylium cations, aluminum cations, ammonium cations, protonated arenes, triaryl carbocation, and other cations which can facilitate a chemical reaction such as a polymerization reaction, coupling reaction, and other catalytic reactions.

Currently, there are no methods to generate stable reactive cations, such as cation-like aluminum (i.e., pseudo aluminum-cation) species, e.g., $AlMe_2^{+1}$, in the presence of weakly coordinating anions (WCA's). For example, when the $AlMe_2^{+1}$ was generated in situ, it caused the rapid decomposition of one of the most efficient WCA's known, viz. $B(C_6F_5)_4^{-1}$ ($Al(C_6F_5)_3$ was one of the reaction products). Other cationic aluminum complexes are based on the use of bulky nitrogen ligands to stabilize the positive charge on the aluminum atom. The synthesis and characterization of aluminum alkyl complexes containing guanidimates,[2] amidinates,[3] aminotroponimates,[4] and pyridyliminoamide[5] ligands have recently been reported. These complexes exhibited ethylene polymerization activity of 900–2,600 g PE/(mol·atm·h) in toluene at 80 to 100° C. and 1 to 5 atm of ethylene.[1,4] However, the steric or electronic properties of the nitrogen ligands may disfavor the coordination and activation of large organic molecules. The synthesis of π-stabilized $(\eta^5-Cp^*)_2Al^{+1}$ has also been reported.[6]

In addition, it is believed no examples of C—H activation by cationic aluminum complexes has been reported. However, $\eta^1$-arene complex of $Al(C_6F_5)_3$ has recently been reported[7], which may represent a model for the first step in C—H activation of aromatic molecules by aluminum cationic complexes. The catalytic activation of aromatic C—H bonds resulting in arene-olefin coupling is of considerable current interest for chemical and pharmaceutical industries.[8,9] Efficient palladium-catalyzed oxidative coupling of arenes with olefins has recently been reported.[8] Other methods of arene-olefin coupling include use of strong Lewis acids (e.g., $AlCl_3$) and Bronsted acids (e.g., HF, $BF_3\cdot HF$, and $AlCl_3\cdot HCl$).[10] However these methods are usually accompanied by isomerization, disproportionation, and transalkylation. In addition, the use of WCA's other than fluorocarborate anions such as $1\text{-R}-CB_{11}F_{11}^{-1}$ to generate $AlMe_2^{+1}$ cation-like species has resulted in rapid decomposition of the aluminum cation as well as the WCA. Furthermore, it is believed that no other stable aluminum compound can catalyze C—H activation in the absence of a strong Bronsted acid.

Furthermore, many conventional co-catalysts for an α-olefin (e.g., ethylene) polymerization, including methylalumoxane (MAO), have limited solubilities in aliphatic hydrocarbon solvents and are not stable when stored in solution.[11]

Therefore, there is a need for stable weakly coordinating anion salts comprising a reactive cation that are useful in variety of organic reactions.

SUMMARY OF THE INVENTION

The present invention provides a compound of the formula:

$$M_xQ_y \qquad\qquad I$$

where each M is independently a cation, provided at least one M is a reactive cation. Preferably, M is selected from the group consisting of silver cation, aluminum cations, silylium cations, ammonium cations, protonated arenes, and triaryl carbocation. Q is a weakly coordinating anion (i.e., WCA). Preferably, Q is a polyhalogenated polyhedral borate or a fluorinated WCA, and more preferably a polyhalogenated polyhedral borate or a fluorinated polyhedral borate moiety selected from the group consisting of monoheteroborate and aminoborate. Preferably, when Q is a monoheteroborate then M is an aluminum cation. The variable x is an absolute value of the oxidation state of Q, i.e., when the oxidation state of Q is −1, then x is 1, and similarly when the oxidation state of Q is −2, then x is 2. Preferably, the oxidation state of Q is −1 or −2. And the variable y is an absolute value of the oxidation state of M. It should be appreciated that when there is more than one type of M is present in the Compound of Formula I, the variable y is the absolute value of the total oxidation states of all M's present. And similarly, when there is more than one type of Q is present in the Compound of Formula I, the variable x is the absolute value of the total oxidation states of all Q's present.

Preferably, the aluminum cation is a moiety of the formula $(R^1R^2Al)^{+1}$, where each of $R^1$ and $R^2$ is independently selected from the group consisting of alkyl, cycloalkyl, aryl, aralkyl, cycloalkalkyl, alkenyl, and halide. Preferably, each of $R^1$ and $R^2$ is independently selected from the group consisting of alkyl, aryl, and halide. And more preferably, each of $R^1$ and $R^2$ is independently selected from the group consisting of methyl, ethyl, iso-propyl, propyl, butyl, iso-butyl, t-butyl, pentyl, hexyl, and halide.

Preferably, the silylium cation is a moiety of the formula $(R^3R^4R^5Si)^{+1}$, where each of $R^3$, $R^4$, and $R^5$ is independently selected from the group consisting of hydrogen, alkyl, aryl, aralkyl, cycloalkyl, and halide. More preferably, each of $R^3$, $R^4$, and $R^5$ is independently selected from the group consisting of hydrogen, alkyl, and aryl. And most preferably, each of $R^3$, $R^4$, and $R^5$ is independently selected from the group consisting of alkyl and aryl.

Preferably, the ammonium cation is a moiety of the formula $(R^{16}R^{17}R^{18}NH)^{+1}$, where each of $R^{16}$, $R^{17}$, and $R^{18}$ is independently selected from the group consisting of hydrogen, alkyl, aryl, aralkyl, cycloalkyl, and silyl. Preferably, each of $R^{16}$, $R^{17}$, and $R^{18}$ is independently selected from the group consisting of alkyl, aryl, aralkyl, and cycloalkyl. More preferably, $R^{16}$, $R^{17}$, and $R^{18}$ are alkyl.

Preferably, the protonated arene is a moiety of the formula $(Ar^1H)^{+1}$, where $Ar^1$ is an optionally substituted aryl. In one embodiment of the present invention, $Ar^1$ is phenyl.

Preferably, the triaryl carbocation is a moiety of the formula $(Ar^2Ar^3Ar^4C)^{+1}$, where each of $Ar^2$, $Ar^3$, and $Ar^4$ is independently an optionally substituted aryl. In one embodiment of the present invention, $Ar^2$, $Ar^3$, and $Ar^3$ are phenyl (i.e., the triaryl carbocation is trityl cation).

Preferably, the monoheteroborate anion is of the formula $((R^6)_aZB_bH_cF_dX_e(OR^7)_f)^{-1}$, where $R^6$ is bonded to Z, Z is bonded to B, and each of H, F, X, and $OR^7$ is bonded to a different boron atom. $R^6$ is selected from the group consisting of polymer, hydrogen, halide, alkyl, silyl, cycloalkyl, alkenyl, alkynyl, and aryl. Preferably, $R^6$ is selected from the group consisting of alkyl, aryl, and sily. More preferably $R^6$ is selected from the group consisting of methyl, ethyl, dodecyl, butyl, iso-butyl, t-butyl, silyl, propyl, iso-propyl, pentyl, hexyl, and a polymer. Z is selected from the group consisting of C, Si, Ge, Sn, Pb, N, P, As, Sb, and Bi. Preferably Z is C. Each X is independently halide. $R^7$ is selected from the group consisting of polymer, hydrogen, alkyl, cycloalkyl, alkenyl, alkynyl, and aryl. The variable "a" is 0 or, preferably, 1. The variable "b" is an integer from 5 to 13, preferably 11. The variable "c" is an integer from 0 to 12, preferably c" is 0. The variable "d" is an integer from 2 to 13, preferably 11. The variable "e" is an integer from 0 to 11, preferably 0. And the variable "f" is an integer from 0 to 5, preferably 0. The sum of c+d+e+f is b.

Preferably, the aminoborate anion is a moiety of the formula $(R^8R^9R^{10}NB_gH_hF_i)^{-1}$, where $R^8$, $R^9$, and $R^{10}$ are bonded to N, and N is bonded to boron, and each of H and F is bonded to a different boron atom. Each of $R^8$, $R^9$, and $R^{10}$ is independently selected from the group consisting of hydrogen, alkyl, cycloalkyl, aryl, aralkyl, and a polymer. Preferably, $R^8$, $R^9$, and $R^{10}$ are alkyl. The variable "g" is an integer from 6 to 14, preferably 12. The variable "h" is an integer from 0 to 13, preferably 0. The variable "i" is an integer from 1 to 14, preferably 11. And the sum of 1+h+i is g.

Preferably, the polyhalogenated borate anion is a moiety of the formula $(B_{12}X_{12})^{-2}$, where each X is independently halide. Preferably the halide of polyhalogenated borate is selected from the group consisting of Cl and F. In one particular embodiment of the present invention, the polyhalogenated borate comprises at least three fluorine atoms, preferably at least 6 fluorine atoms, more preferably at least 11 fluorine atoms, and most preferably all of the X are fluorine atoms.

One particular embodiment of the present invention provides a compound of the formula:

$$M^1_m(R^1R^2Al)_nQ_q \qquad \text{IA}$$

where $R^1$, $R^2$, and Q are those defined above; $M^1$ is a non-reactive cation; m is 0 or 1; n is 1 or 2, provided that the sum of m and n is an absolute value of the oxidation state of Q; and q is an absolute value of the total oxidation state of $M^1$ and ($R^1R^2Al$), preferably q is 1 or 2, and more preferably q is 1.

Another aspect of the present invention provides a catalyst component comprising the Compound of Formula I.

In one particular embodiment of the present invention, the catalyst component comprises a compound selected from compounds of the formula:

$(R^1R^2Al)((R^6)_aZB_bH_cF_dX_e(OR^7)_f);$     (i)

$(R^3R^4R^5Si)((R^6)_aZB_bH_cF_dX_e(OR^7)_f);$     (ii)

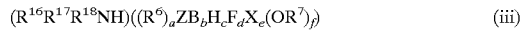

$(R^{16}R^{17}R^{18}NH)((R^6)_aZB_bH_cF_dX_e(OR^7)_f)$     (iii)

$(Ar^1H)((R^6)_aZB_bH_cF_dX_e(OR^7)_f);$     (iv)

$(Ar^2Ar^3Ar^4C)((R^6)_aZB_bH_cF_dX_e(Or^7)_f);$     (v)

and $Ag((R^6)_aZB_bH_cF_dX_e(OR^7)_f),$     (vi)

where $Ar^1$, $Ar^2$, $Ar^3$, $Ar^4$, $R^1$, $R^2$, $R^3$, $R^4$, $R^5$, $R^6$, $R^7$, $R^{16}$, $R^{17}$, $R^{18}$, Z, X, a, b, c, d, e, and f are those defined above.

In another embodiment of the present invention, the catalyst component comprises a compound selected from compounds of the formula:

$(R^1R^2Al)(R^8R^9R^{10}NB_gH_hF_i);$     (i)

$(R^3R^4R^5Si)(R^8R^9R^{10}NB_gH_hF_i);$     (ii)

$(R^{16}R^{17}R^{18}NH)(R^8R^9R^{10}NB_gH_hF_i)$     (iii)

$(Ar^1H)(R^8R^9R^{10}NB_gH_hF_i);$     (iv)

$(Ar^2Ar^3Ar^4C)(R^8R^9R^{10}NB_gH_hF_i);$     (v)

and $Ag(R^8R^9R^{10}NB_gH_hF_i),$     (vi)

where $Ar^1$, $Ar^2$, $Ar^3$, $Ar^4$, $R^1$, $R^2$, $R^3$, $R^4$, $R^5$, $R^8$, $R^9$, $R^{10}$, $R^{16}$, $R^{17}$, $R^{18}$, g, h, and i are those defined above.

Yet in another embodiment of the present invention, the catalyst component comprises a compound selected from compounds of the formula:

$(M^1)_m(R^1R^2Al)_n(B_{12}X_{12});$     (i)

$(M^1)_m(R^3R^4R^5Si)_n(B_{12}X_{12});$     (ii)

$(M^1)_m(R^{16}R^{17}R^{18}NH)_n(B_{12}X_{12})$     (iii)

$(M^1)_m(Ar^1H)_n(B_{12}X_{12});$     (iv)

$(M^1)_m(Ar^2Ar^3Ar^4C)_n(B_{12}X_{12});$     (v)

and $(M^1)_mAg_n(B_{12}X_{12}),$     (vi)

where $Ar^1$, $Ar^2$, $Ar^3$, $Ar^4$, $R^1$, $R^2$, $R^3$, $R^4$, $R^5$, $R^{16}$, $R^{17}$, $R^{18}$, $M^1$, X, m, and n are those defined above.

Still another aspect of the present invention provides a process for preparing an olefin polymer by polymerization of at least one olefin compound in the presence of a catalyst component, where the catalyst component comprises the Compound of Formula I described above. Preferably, the olefin is an α-olefin.

Yet another aspect of the present invention provides an arene-olefin coupling process using the Compound of Formula IA.

Still another aspect of the present invention provides a method for preparing the Compound of Formula I.

DETAILED DESCRIPTION OF THE INVENTION

Figure 1:
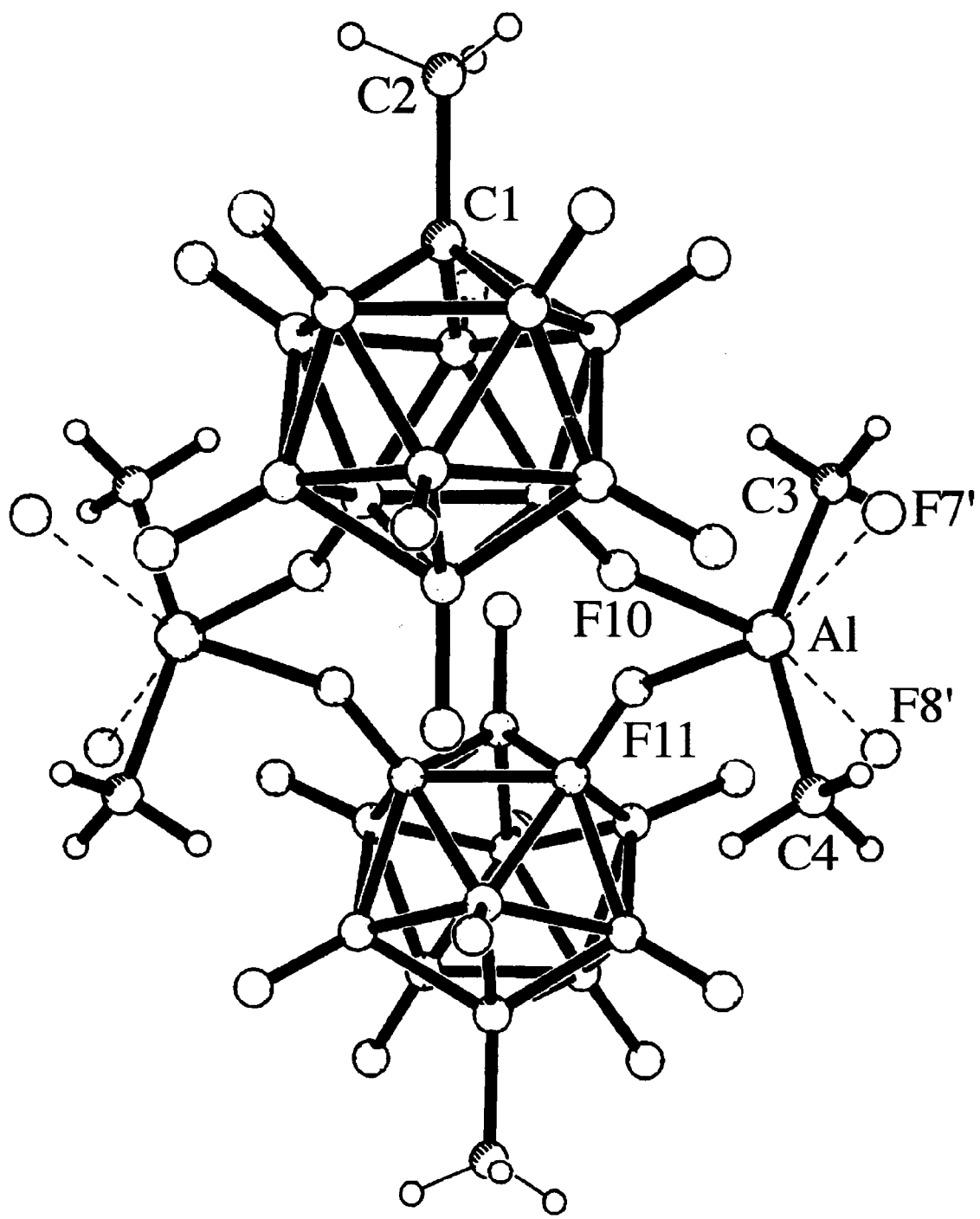
FIG. 1 is an x-ray crystal structure of $[Al(CH_3)_2(1\text{-}CH_3\text{—}CB_{11}F_{11})]_2$.
Figure 2:
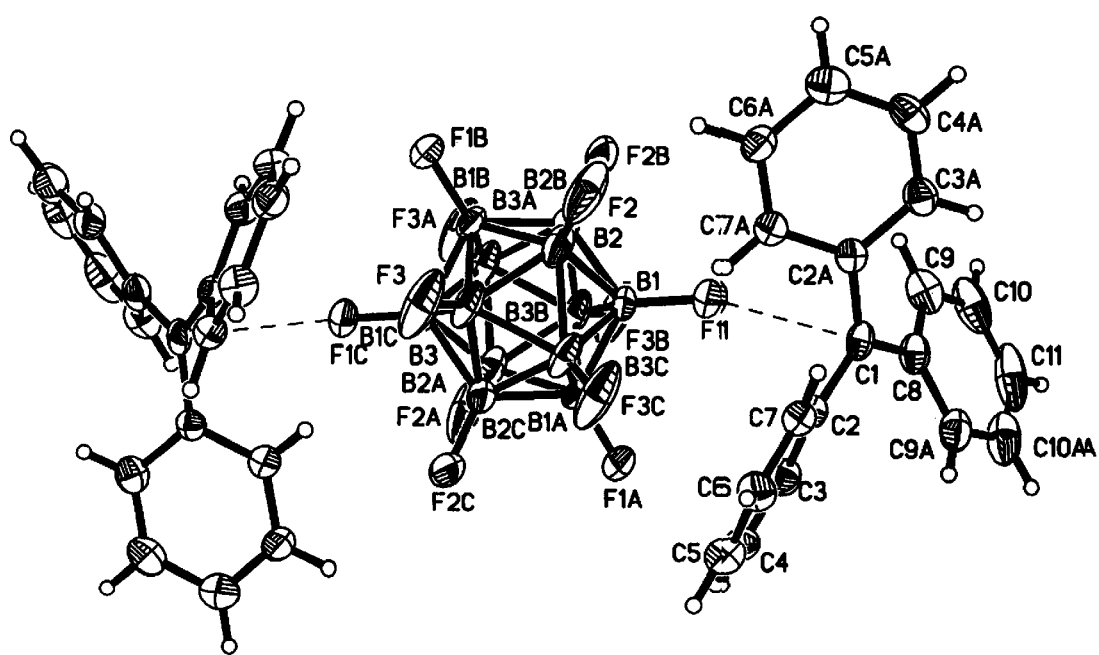
FIG. 2 is an x-ray crystal Structure of $(CPh_3)_2B_{12}F_{12}$.
Figure 3:
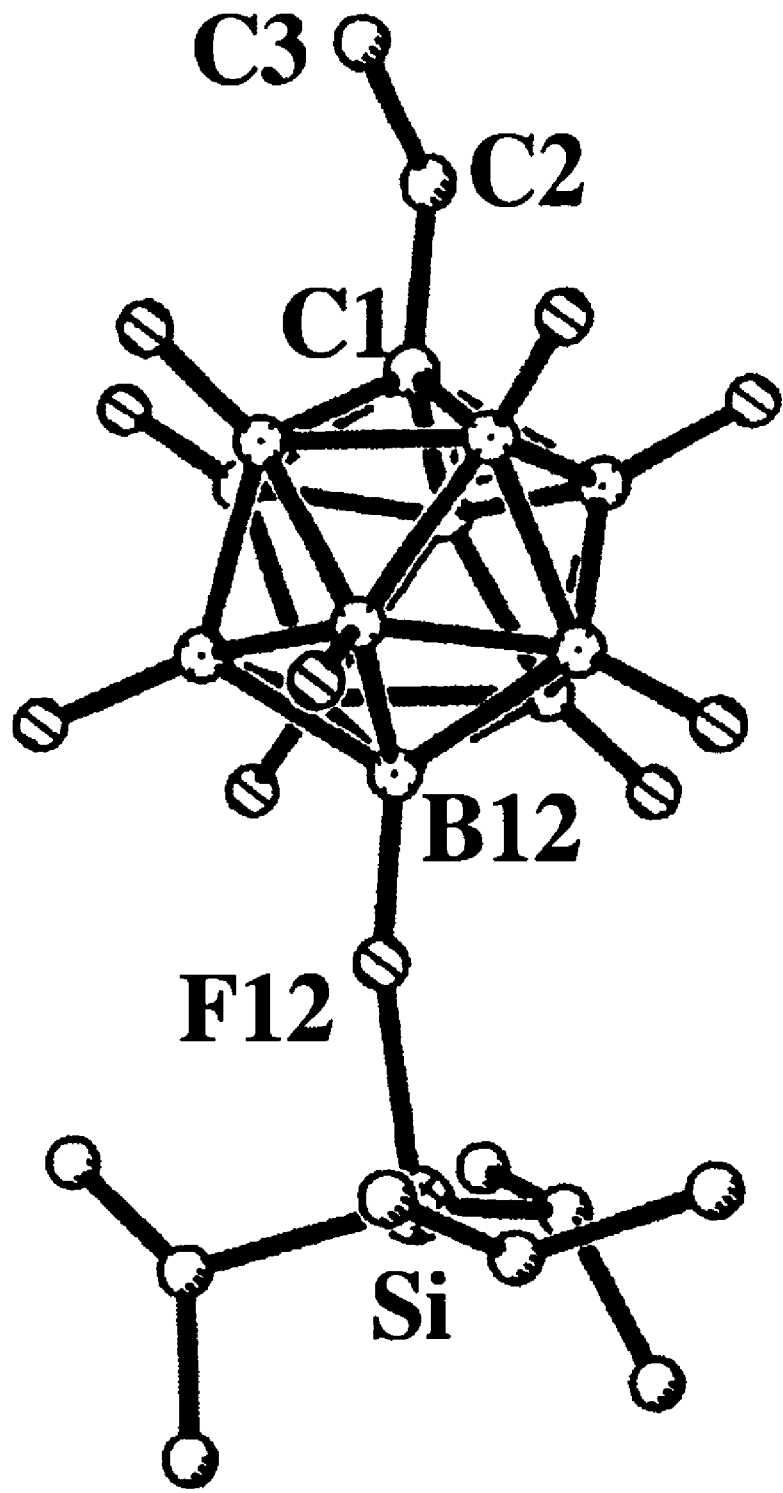
FIG. 3 is an x-ray crystal Structure of $Si(i\text{-}Pr)_3(1\text{-}Et\text{-}CB_{11}F_{11})$

The term "alkyl" refers to aliphatic hydrocarbons which can be straight or branched chain groups. Preferably an alkyl group has one to about twenty carbon atoms. Alkyl groups optionally can be substituted with one or more substituents, such as a halogen, alkenyl, alkynyl, aryl, hydroxy, amino, thio, alkoxy, carboxy, oxo or cycloalkyl. There may be optionally inserted along the alkyl group one or more oxygen, sulfur or substituted or unsubstituted nitrogen atoms. Exemplary alkyl groups include methyl, ethyl, n-propyl, i-propyl, n-butyl, t-butyl, pentyl, octyl, dodecyl, fluoromethyl, difluoromethyl, trifluoromethyl, chloromethyl, trichloromethyl, pentafluoroethyl, and the like.

The term "halo," "halide" or "halogen," when referring to a substituent means fluoro, chloro, bromo, or iodo, preferably chloro or fluoro.

The term "cycloalkyl" refers to a saturated monovalent substituted or unsubstituted mono- or bicyclic hydrocarbon or heterocycle radical, preferably of three to twenty carbon atoms. Cycloalkyl may contain one, two or three substituents which are not hydrogen. Exemplary cycloalkyls include, but are not limited to, substituted or unsubstituted cyclopropyl, cyclopentyl, cyclohexyl, cyclooctyl, bicyclodecyl, and the like.

The terms "aryl" and "arene" refers to a monovalent monocyclic or bicyclic aromatic hydrocarbon radical which is optionally substituted with one or more substituents, preferably of five to 20 carbon atoms. Exemplary aryls or arenes include, but is not limited to, substituted or unsubstituted phenyl, substituted or unsubstituted 1-naphthyl, 2-naphthyl, and the like.

The term "heterocycle" means a substituted or unsubstituted saturated cyclic radical in which one or two ring atoms are heteroatoms selected from the group consisting of N, O, or $S(O)_n$ (where n is an integer from 0 to 2), the remaining ring atoms being C. The heterocycle ring may be optionally substituted independently with one, two, or three substituents such as alkyl, alkoxy, and aryl groups.

As used herein, the term "heteroalkyl" means a branched or unbranched, cyclic or acyclic saturated alkyl radical containing carbon, hydrogen and one or more heteroatoms in place of a carbon atom, or optionally one or more heteroatom-substituents containing carbon atom.

The term "aralkyl" means a radical —$R^aR^b$ where $R^a$ is an alkylene group and $R^b$ is an aryl group as defined above, e.g., benzyl, phenylethyl, and the like.

The term "cycloalkylalkyl" means a radical —$R^aR^b$ where $R^a$ is an alkylene group and $R^b$ is a cycloalkyl group as defined above, e.g., cyclopropylmethyl, cyclopentylmethyl, cyclohexylmethyl, and the like.

The terms "alkoxy", "aryloxy", "aralkyloxy", and "heteroaralkyloxy" mean a radical —OR where R is an alkyl, aryl, aralkyl, and heteroaralkyl, respectively, as defined above, e.g., methoxy, phenoxy, pyridin-2-ylmethyloxy, benzyloxy, and the like.

The term "reactive cation" refers to a cation which can facilitate a chemical reaction such as a polymerization reaction, coupling reaction, and other catalytic reactions. Exemplary reactive cations include silver cation, aluminum cations, silylium cations, ammonium cations, protonated arenes, and triaryl carbocation.

The term "weakly coordinating anion" refers to the anion which weakly coordinates to a reactive cation and can be easily displaced from the cation by neutral donor molecules.

The term "pseudohalide" refers to moieties which are not halides but are generally considered to be a good leaving group in a substitution reaction. Exemplary pseudohalides include isocyanate, cyanide, tosylate, mesylate, acetate, and the like.

Unless otherwise defined, the term "silyl" refers to a moiety of the formula $R^aR^bR^cSi$—, where each of $R^a$, $R^b$, and $R^c$ is independently hydrogen, alkyl, aryl, aralkyl, or cycloalkyl.

The present invention provides salts comprising a weakly coordinating anion and a reactive cation, and catalyst components comprising the same. The present invention also provides methods for preparing these salts as well as methods for using these salts. In particular, the present invention provides fluoroborate salts comprising a reactive cation.

In one aspect, the present invention provides compounds of the formula:

$$M_xQ_y \qquad\qquad\qquad I$$

where M, Q, x, and y are those defined above. It should be appreciated that when the oxidation state of Q is –2, then x is 2. In such cases, more than one M moiety can be present. Preferably at least one M moiety is a reactive cation. The other M moiety can be any cation such as an alkaline metal (e.g., Li, Na, K, Rb, Cs, or Fr) or a transition metal cation (e.g., $Cu^{+1}$, $Ag^{+1}$, $Ni^{+2}$, $Zn^{+2}$, $Pd^{+2}$).

One aspect of the present invention provides cations comprising an aluminum, which are useful in a variety of organic reactions, including as catalysts for the activation of carbon-hydrogen bonds and as co-catalysts for the polymerization of olefins, in particular, α-olefins such as ethylene. The present invention also provides a method for preparing the same.

In one embodiment, the present invention provides a compound of the formula:

$$M^1{}_m(R^1R^2Al)_nQ_q \qquad\qquad\qquad IA$$

where $R^1$, $R^2$, Q, $M^1$, m, n, and q are those defined above. Compound of Formula IA comprises a very chemically robust (i.e., stable) weakly coordinating anion, Q, which does not readily decompose. In addition, unlike many other aluminum metal catalysts, Compound of Formula IA has a relatively high solubility in aliphatic hydrocarbon solvents. For example, the compound $AlMe_2(1\text{-}Dd\text{-}CB_{11}F_{11})$, where Dd is dodecyl, is soluble in hexanes and methylcyclohexane and stable for at least 10 days at 25° C. Moreover, it has been shown to be a good co-catalyst for metallocene catalyzed olefin, e.g., ethylene, polymerization.

Preferably each of $R^1$ and $R^2$ is independently selected from the group consisting of alkyl and aryl. More preferably, each of $R^1$ and $R^2$ is independently selected from the group consisting of methyl, ethyl, phenyl, halide, and pseudohalide.

In one particular embodiment of the present invention, the compound of the present invention is of the formula:

$$(R^1R^2Al)[(R^6)_aZB_bH_cF_dX_e(OR^7)_f] \qquad\qquad\qquad II$$

where $R^1$, $R^2$, $R^6$, $R^7$, X, Z, a, b, c, d, e, and f are those defined above.

With respect to Compounds of Formula II:

Preferably, each X is independently halide. More preferably, X is selected from the group consisting of chloride, iodide, and bromide, still more preferably X is selected from the group consisting of chloride and bromide, and most preferably X is chloride.

Preferably, $R^7$ is selected from the group consisting of polymer, alkyl, cycloalkyl, and aryl. More preferably, $R^7$ is selected from the group consisting of polymer, alkyl, and aryl. And most preferably, $R^7$ is an alkyl.

Preferably, a is 1.

Preferably, b is an integer from 5 to 11. More preferably b is 5, 9 or 11, still more preferably b is 9 or 11, and most preferably b is 11.

Preferably, c is an integer from 0 to 7, more preferably from 0 to 5, and most preferably 0.

Preferably d is an integer from 2 to 13, more preferably from 2 to 11. Still more preferably d is 5, 9 or 11, yet still more preferably d is 9, or 11, and most preferably d is 11.

Preferably, e is an integer from 0 to 11, and more preferably from 0 to 5. Most preferably e is 0.

Preferably, f is an integer from 0 to 5, more preferably from 0 to 4, and most preferably from 0 to 3.

In another embodiment, the compound of the present invention is of the formula:

$$(R^1R^2Al)[R^{11}R^{12}R^{13}N\text{—}B_gH_hF_i] \quad \text{II}$$

where $R^1$, $R^2$, $R^{11}$, $R^{12}$, $R^{13}$, g, h, and i are those defined above.

With respect to Compounds of Formula III:

Preferably, each of $R^{11}$, $R^{12}$, and $R^{13}$ is independently selected from the group consisting of hydrogen, methyl, ethyl, butyl, benzyl, hexyl, cyclohexylmethyl, octyl, dodecyl, and silyl.

Preferably, the variable g is 10 or 12. More preferably g is

Preferably, h is 0.

Preferably, i is g−1 (i.e., when g is 10 or 12, i is 9 or 11, respectively).

Compounds of Formula IA can be prepared by a variety of methods. In one specific example, Compounds of Formula II can be prepared according to the following reaction equation:

$$\text{AlMe}_3 + \text{[CPh}_3^+\text{][1-Me-CB}_{11}\text{F}_{11}^{-1}\text{]} \longrightarrow \text{AlMe}_2(\text{1-Me-CB}_{11}\text{F}_{11}) + \text{CH}_3\text{CPh}_3 \quad (\text{eq. 1})$$

1
2
3
4

Briefly, a trisubstituted aluminum compound (e.g., Compound 1) is reacted with a compound containing a WCA (e.g., Compound 2). One of the substituent in the trisubstituted aluminum compound is displaced by the WCA to produce Compound of Formula II (e.g., Compound 3) and a cation-substituent coupled product (e.g., Compound 4) which is formed from the counter cation (e.g., trityl group in the above equation) of compound containing WCA and the displaced substituent of the trisubstituted aluminum compound.

Without being bound by any theory, it is believed that the first step in the reaction is displacement of the counter cation of compound containing WCA by trisubstituted aluminum compound. It is believed that the displaced cation then reacts with one of the substituent on the trisubstituted aluminum moiety to generate Compound of Formula II and the cation-substituent coupled product. Moreover, it is generally believed that stable counter cations of WCA are relatively easily displaced by the trisubstituted aluminum compound.

Because a trisubstituted aluminum compound is generally more readily available and less expensive than other compounds containing WCA, Compound of Formula IA formation reaction generally uses at least 1 equivalents of the trisubstituted aluminum compound relative to the compound containing WCA. Preferably the amount of trisubstituted aluminum compound used in Compound of Formula IA formation reaction is from about 1 equivalents to about 15 equivalents, more preferably from about 2 equivalents to about 10 equivalents, and most preferably from about 2 equivalents to about 5 equivalents.

When $\text{AlMe}_2(1\text{-Me}\text{—}\text{CB}_{11}\text{F}_{11})$, which can be prepared as shown in eq. 1 above, was dissolved in toluene-d8, formation of mono-deuteromethane, $\text{CH}_3\text{D}$, was observed. Without being bound by any theory, it is believed that this may have occurred by activation of one of the aromatic C—D bonds of the solvent $\text{C}_6\text{D}_5\text{CD}_3$, as shown in the reaction equation below:

$$\text{AlMe}_2(1\text{-Me}\text{—}\text{CB}_{11}\text{F}_{11}) + 2\, \text{C}_6\text{D}_5\text{CD}_3 \rightarrow \text{Al}(\text{C}_6\text{D}_4\text{CD}_3)_2(1\text{-Me}\text{—}\text{CB}_{11}\text{F}_{11}) + 2\, \text{CH}_3\text{D}$$

This reaction constitutes stoichiometric activation of aromatic C—H (in this case C—D) bonds.

Compounds of Formula IA are useful in a variety of organic reactions including in an arene-olefin coupling reaction. Thus, when the above reaction was repeated under one atmosphere of ethylene ($\text{CH}_2\text{=CH}_2$), a GC-MS analysis of the reaction mixture after 14.5 hr at 24° C. indicated the catalytic formation of all three positional isomers (i.e., the ortho (47%), meta (35%), and para (18%) isomers) of $\text{C}_6\text{D}_4(\text{CD}_3)(\text{CH}_2\text{CH}_2\text{D})$ (the number of turnovers in this particular experiment was approximately 60–70. Without being bound any theory, the proposed catalytic scheme, which includes the catalytic activation of aromatic C—H bonds and the catalytic insertion of ethylene into an aluminum-aryl bond, is shown in FIG. 1 in a generic scheme using $\text{C}_6\text{H}_6$ as the substrate instead of $\text{C}_6\text{D}_5\text{CD}_3$ for simplicity (the coordinated fluorocarborate anion (i.e., Q moiety) has also been omitted from the scheme for simplicity). It should be appreciated that the $\text{AlPh}_2^{+1}$ species shown in FIG. 1 may in fact be a mixture of $\text{AlPh}_2^{+1}$ and $\text{AlMePh}^{+1}$ species.

When toluene-d8 was used as the substrate, the aryl aluminum moiety at the top of the central cycle in FIG. 1 is one of the three possible isomers shown below, which accounts for the three isomers of $\text{C}_6\text{D}_4(\text{CD}_3)(\text{CH}_2\text{CH}_2\text{D})$ observed in the GC-MS analysis (R=o-, m-, or p-tolyl group):

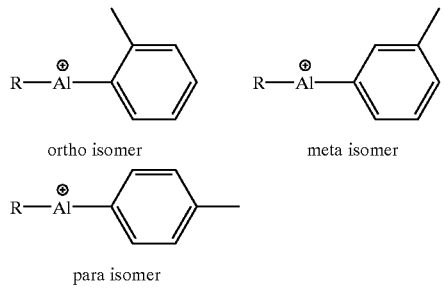

ortho isomer    meta isomer para isomer

Thus, another aspect of the present invention provides a process for coupling an olefin to an aryl compound comprising:

(a) contacting an aryl compound of the formula:

$$R^{11}H$$

with Compound of Formula IA to form a hydrocarbylaluminum complex selected from the group consisting of a compound of the formula:

$M^1_m(R^1R^{11}Al)_nQ_q$, $M^1_m(R^2R^{11}Al)_nQ_q$, $M^1_m[R^{11})_2Al]_nQ_q$, and mixtures thereof, and (b) contacting the hydrocarbylaluminum complex with an olefin of the formula:

$R^{12}R^{13}C=CR^{14}R^{15}$ to form an alkyl substituted aryl compound of the formula:

$R^{11}R^{12}R^{13}C—CHR^{14}R^{15}$ where $R^1$, $R^2$, Q, $M^1$, m, n, and q are those defined above. And where $R^{11}$ is an aryl, preferably phenyl, toluyl, or xylyl. Preferably $R^{11}$ is substituted or unsubstituted phenyl. Each of $R^{12}$, $R^{13}$, $R^{14}$ and $R^{15}$ is independently selected from the group consisting of hydrogen, alkyl, aryl, cycloalkyl, aralkyl, cycloalkakyl, halide, and a polymer. Preferably, each of $R^{12}$, $R^{13}$, $R^{14}$ and $R^{15}$ is independently selected from the group consisting of hydrogen, alkyl, aryl, cycloalkyl, aralkyl, cycloalkakyl, and halide.

The arene-olefin coupling is preferably carried out at a temperature of from about −90° C. to about 300° C., particularly preferably from about 0 to about 140° C. The reaction pressure is from about 100 mmHg to about 100000 mmHg, preferably from about 500 mmHg to about 10000 mmHg. The arene-olefin can be carried out continuously or batchwise, in one or more stages, in solution, in suspension, in the gas phase or in a supercritical medium.

It is also possible to use mixtures of two or more Compounds of Formula IA. Moreover, the Compounds of Formula IA (or Compounds of Formula I comprising the polyhedral borate anion, in particular a monoheteroborate) can also be applied to a solid support. Exemplary solid support materials which are useful in the present invention include, but not limited to, activated carbon, alumina, silica, zeolites and polymeric supports. Exemplary polymeric supports include polymer resins such as polystyrene, polyethylene, polyurethane, polypropylene, and polytetrafluoroethylene. Typically, in an arene-olefin coupling reaction, the Compound of Formula IA is used in a concentration of preferably from about 0.01 mM to about 1 M, more preferably from about 1 mM to about 100 mM.

More generally, Compounds of Formula I can be prepared by:

(i) fluorinating a non-fluorinated compound of the formula $M^1_pQ^1_q$ by contacting the non-fluorinated compound with HF, $F_2$ or mixtures thereof under conditions sufficient to produce a fluorinated salt of the formula $M^1_pQ^2_q$, where $M^1$ is that defined above; $Q^1$ is a nonfluorinated polyhedral borate moiety selected from the group consisting of monoheteroborate, aminoborate, and polyhalogenated borate; $Q^2$ is a fluorinated $Q^1$; p is an absolute value of the oxidation state of $Q^1$; and q is an absolute value of the oxidation state of $M^1$, and (ii) exchanging the non-reactive cation with a reactive cation to produce a fluorinated salt of the formula $M_pQ^2_q$, where M, Q, p, and q are those defined above.

Fluorination of a non-fluorinated compound of the formula $M^1_pQ^1_q$ are generally described in commonly assigned U.S. patent application Ser. No. 09/049,420, now U.S. Pat. No. 6,130,357, issued Oct. 10, 2000, which is incorporated herein by reference in its entirety. Procedures for fluorinating a non-fluorinated Compound of the Formula $M^1_pQ^1_q$ can also be found in commonly assigned U.S. patent application Ser. No. 09/704,252 entitled "Fluorinated Amino Polyhedral Boron Compounds", filed even date herewith, which is incorporated herein by reference in its entirety.

The work-up of fluorination reaction mixtures typically results in the isolation of cesium, potassium, or trimethylammonium salts of fluorinated anions. The work-up of alkylation reactions of fluorinated aminoborate anions usually results in the isolation of cesium or tetraalkylammonium salts. A variety of different methods are available to convert the above salts into the salts of fluorinated polyhedral borate anions with reactive cations, such as trialkylammonium, silver, triaryl carbocation, silylium, dialkylaluminum and others. Tetraalkylammonium, cesium, and potassium salts of fluorinated borate and carborane anions can be converted into acids $H_xQ.(solvent)_z$, where $x$ and Q are those defined above and z is the amount of solvation, by eluting their solutions through a column packed with a cation exchange resin in its acidic form. Suitable solvents include an aqueous solvent and polar organic solvents, such as methanol, acetonitrile and others. The acids $H_xQ.(solvent)$ can be neutralized with $(M^3)^+(OH)^-(M^3$=metal) or appropriate amines $R^{16}R^{17}R^{18}N$, where $R^{16}$, $R^{17}$ and $R^{18}$ are those defined above, to prepare metal salts $M^3_2Q.(solvent)_z$ or trialkylammonium salts $(R^{16}R^{17}R^{18}NH)(Q)$ of fluorinated polyhedral borate anions. Trialkylammonium salts of fluorinated polyhedral borate and carborane anions can also be prepared by the metathesis reactions of potassium, cesium, or silver salts of fluorinated borate and carborane anions with trialkylammonium halides. The separation of the products from the reaction mixtures is usually much easier if the silver salts of fluorinated borate and carborane anions are used for the metathesis reactions.

The silver salts of fluorinated borate and carborane anions can be prepared by the metathesis reactions of their cesium and potassium salts with silver tetrafluoroborate in appropriate organic solvents. Preferably the cesium or potassium salts of fluorinated borate and carborane anions is soluble in that solvent and cesium or potassium salts of tetrafluoroborate anion is insoluble or only very slightly soluble in that solvent. Suitable solvents for the preparation of silver salts include acetonitrile, dichloromethane, benzene, toluene, ether, tetrahydrofuran and other solvents, which satisfy the above requirements. Depending on the solvent, the isolation of the silver complexes with solvent molecules or the neat silver salts is possible.

There are a variety of methods for the syntheses of triaryl carbocation salts with fluorinated polyhedral borate anions. For example, the salts of fluorinated polyhedral borate anions comprising an electrophilic cation, such as $Li^+$ or $Ag^+$, can be treated with a triaryl carbon halide, e.g., $CPh_3Cl$, in an appropriate organic solvent. Without being bound by any theory, it is believed that the reaction is based on the halide abstraction from the triaryl carbon halide by the electrophilic cation. The insoluble lithium or silver halides are removed by filtration and triaryl carbocation salts are isolated from the filtrate. Suitable solvents for the preparation of triaryl carbocation salts include acetonitrile, dichloromethane, benzene, toluene, ether, tetrahydrofuran and other organic solvents. Alternatively, triaryl carbocation salts can be prepared by the metathesis reactions of cesium or potassium salts of fluorinated polyhedral borate anions with a triaryl carbocation tetrafluoroborate. Cesium or potassium salts of tetrafluoroborate are removed from the reaction mixtures by filtration and triaryl carbocation salts of fluorinated borate and carborane anions are isolated from the filtrate.

The syntheses of silylium and dialkylaluminum salts of fluorinated borate and carborane anions usually require the use of their triarylcarbenium salts, preferentially triaryl carbocation salts, as a starting material. The syntheses involve treatment of trialkylsilanes and alkylaluminum compounds with a triaryl carbocation salt of fluorinated polyhedral borate anion. Without being bound by any theory, the synthetic strategy is based on the formation of stronger C—H or C—C bonds compare to relatively weaker Si—H or Al—C bonds. In the reactions of trityl cation salts with trialkylsilanes, the hydride abstraction by trityl cation is believed to occur to form triphenylmethane. In the reaction of trityl salts with alkylaluminum compounds, the hydride or alkyl abstractions can occur depending on the structure of alkylaluminum compound as shown below:

$$R^3R^4R^5SiH+(trityl)Q \rightarrow (R^3R^4R^5Si)(Q)+(trityl)H$$

$$R^1R^2AlR^{19}+(trityl)Q \rightarrow (R^1R^2Al)(Q)+(trityl)R^{19}$$

where $R^1$, $R^2$, $R^3$, $R^4$, $R^5$, $R^{19}$, and Q are those defined above.
For example:

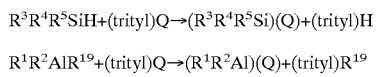

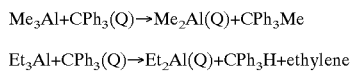

The choice of the solvent facilitates production and isolation of products in the above reactions since the generated silylium and diallylaluminum cations are highly reactive and typically form strong complexes with oxygen or nitrogen containing solvents and also abstract halogen atoms from halogenated solvents. Preferred solvents include hydrocarbon organic solvents (i.e., compounds having only carbon and hydrogen atoms), such as benzene, toluene, xylene, pentane, hexane, isooctane and others. Preferably, an excess amount of trialkylsilane is used in the preparation of silylium salts of fluorinated polyhedral borate anions.

Generally, Compound of Formula I can be prepared at any temperature in which the starting materials and/or the products are relatively stable. Typically, the reaction temperature for producing Compounds of Formula I is in the range from about −70° C. to about 130° C. Preferably, the reaction temperature is in the range of from about −70° C. to about 100° C., more preferably from about −30° C. to about 70° C., and most preferably from about 0° C. to about 70° C. In one particular embodiment of the present invention, the reaction temperature is at about 40° C. or less, and preferably at about 25° C. or less.

The reaction time can vary depending on a variety of factors including the reaction temperature, a particular reaction solvent and/or starting materials used, the amount of each starting material used, and the concentration of each starting materials. Typically, however, the reaction time is from about 0.5 h to about 48 h, preferably from about 0.5 h to about 40 h, and more preferably from about 1 h to about 24 h.

Because Compounds of Formula I are generally oxygen and/or moisture sensitive, reactions for producing Compound of Formula I are typically conducted under an inert atmosphere, preferably a nitrogen, helium or argon atmosphere.

The present invention also provides a process for preparing an olefin polymer by polymerization of at least one olefin in the presence of a catalyst component comprising the Compound of Formula I. The polymerization can be a homopolymerization or a copolymerization.

Preference is given to polymerizing an α-olefin, i.e., an olefin of the formula $X^aX^bC=CR^aR^b$, where each of $X^a$ and $X^b$ is independently hydrogen or a halide, preferably each of $X^a$ and $X^b$ is independently hydrogen, chloride or fluoride; and each of $R^a$ and $R^b$ is independently hydrogen, halogen, alkyl, aryl, or cycloalkyl. Exemplary α-olefins include, but not limited to, ethylene, propylene, 1-butene, 1-hexene, 4-methyl-1-pentene, 1-octene, styrene, 1,3-butadiene, 1,4-hexadiene, acrylates such as methyl acrylate. Other olefins which can be polymerized using the catalyst component of the present invention include non-α-olefins such as cyclic olefins including, but not limited to, cyclopentadiene norbornene, vinylnorbornene, tetracyclododecene, and ethylidenenorbornene.

The polymerization is preferably carried out at a temperature of from about −70° C. to about 200° C., particularly preferably from about 0 to about 150° C. The polymerization pressure is from about 500 mmHg to about 50000 mmHg, preferably from about 700 mmHg to about 3500 mmHg. The polymerization of an olefin can be carried out continuously or batchwise, in one or more stages, in solution, in suspension, in the gas phase or in a supercritical medium.

In a solution polymerization process, suitable solvents include hydrocarbons such as benzene, toluene, hexane, and isooctane. Preferably, the polymerization solvent is toluene or saturated hydrocarbons. And most preferably, the polymerization solvent is isooctane.

It is also possible to use mixtures of two or more Compounds of Formula I. In addition, Compounds of Formula I can also be applied to a solid support. Exemplary solid support materials which are useful in the present invention include, but not limited to, activated carbon, alumina, silica, zeolites or polymeric supports described above. Typically, in an olefin polymerization, a Compound of Formula I is used in a concentration of preferably from about 1 μM to about 1000 μM, more preferably from about 1 μM to about 100 μM, and most preferably from about 5 μM to about 50 μM.

Prior to addition of the catalyst component, another aluminum alkyl compound, for example, trimethylaluminum, triisobutylaluminum, triethylaluminum, trioctylaluminum, isoprenylaluminum, or alkylaluminoxanes can be added to the reactor to stabilize the polymerization system (for example, for removing catalyst poisons present in the olefin). This is added to the polymerization system in a concentration of from about 0.01 to about 10 mmol per kg of reactor contents. For example, triisobutylaluminum or triethylaluminum in a concentration of from about 0.01 mmol to about 1 mmol per kg of reactor contents is typically added.

Compounds of Formula I are also effective co-catalysts for the most of conventional olefin polymerization catalysts. Exemplary olefin polymerization catalysts, include, but are not limited to, organometallic single site olefin polymerization catalysts, preferably organotransition metal single site olefin polymerization catalysts. As used herein, "organometallic or organotransition metal single site olefin polymerization catalysts" refers to a compound comprising a metal or a transition metal, respectively, which is coordinated to at least one cyclopentadienyl (i.e., Cp) group or its derivative such as metallocenes. In particular organometallic single site olefin polymerization catalysts based on group III, IV, and V metals. The group IV catalysts are typically cationic while the Group III metallocene catalysts are typically neutral. Cationic group IV complexes are usually generated by the reaction of neutral group IV complexes with triaryl carbocation or trialkylammonium salts of weakly coordinating anions or with large excess of methylaluminoxane (MAO) (e.g., >1000 Al per Zr). Compounds of Formula I are generally soluble in aliphatic hydrocarbon solvents and can be used as stoichiometric co-catalysts for group IV catalysts, thus eliminating the need for large excess of MAO. The other examples of olefin polymerization catalysts include cationic nickel, palladium and iron complexes comprising diimine and/or phosphine ligands. Other useful polymerization catalysts are disclosed in, for example, U.S. Pat. No. 5,278,119, which is incorporated herein by reference in its entirety.

Additional objects, advantages, and novel features of this invention will become apparent to those skilled in the art upon examination of the following examples thereof, which are not intended to be limiting.

EXPERIMENTAL

Experiment 1

This example illustrates a method for producing $Al(CH_3)_2(1\text{-}CH_3\text{---}CB_{11}F_{11})$.

A mixture of $[CPh_3][1\text{-}CH_3\text{---}CB_{11}F_{11}]$ (0.300 g, 0.502 mmol) and toluene (2 ml) was treated with a solution of trimethylaluminum $Al(CH_3)_3$ (0.210 g, 2.92 mmol) in 8 ml of toluene. A mixture was stirred under a nitrogen atmosphere for 44 h. During this time a red oil ($[CPh_3][1\text{-}CH_3\text{---}CB_{11}F_{11}]$) was converted into a light yellow solid. The solid was then separated by filtration under a nitrogen atmosphere. The solid was washed 3 times with 1 ml of hexanes and dried under vacuum to provide 0.184 g (89% yield) of $Al(CH_3)_2(1\text{-}CH_3\text{---}CB_{11}F_{11})$.

$^{19}F$ NMR (toluene-$d_8$): $\delta$–252.7; $^1H$ NMR (toluene-$d_8$): $\delta$1.47 (3 H), –0.81 (~6 H);

$^{19}F$ NMR (acetonitrile-$d_3$): $\delta$–251.7 (1 F), –256.2 (5 F), –258.1 (5 F);

$^1H$ NMR (acetonitrile-$d_3$): $\delta$1.54 (3 H), –0.74, –0.82, and –0.98 (~6 H total);

$^{11}B$ NMR (acetonitrile-$d_3$): $\delta$–8.5 (1 B), –16.9 (10 B).

Experiment 2

This example illustrates a method for producing a crystalline $Al(CH_3)_2(1\text{-}CH_3\text{-}CB_{11}F_{11})$.

To produce a crystalline $Al(CH_3)_2(1\text{-}CH_3\text{-}CB_{11}F_{11})$ compound the reaction described in the Example 1 is performed without stirring. A solution of trimethylaluminum $Al(CH_3)_3$ (0.016 g) in 0.5 ml of toluene was layered over a mixture of $[CPh_3][1\text{-}CH_3\text{-}CB_{11}F_{11}]$(0.011 g) and 0.5 ml of toluene. X-ray quality crystals grew on standing at 25° C. for four days. The X-ray crystal structure of $Al(CH_3)_2(1\text{-}CH_3\text{-}CB_{11}F_{11})$ is shown in FIG. 1.

Experiment 3

This example illustrates a method for producing $Al(CH_3)_2(1\text{-}C_{12}H_{25}\text{---}CB_{11}F_{11})$, which is highly soluble in aliphatic hydrocarbon solvents (hexanes, methylcyclohexane etc.).

A suspension of $[CPh_3][1\text{-}C_{12}H_{25}\text{---}CB_{11}F_{11}]$(0.030 g, 0.040 mmol) in 1 ml of hexanes was treated with a solution of trimethylaluminum $Al(CH_3)_3$ (0.010 g, 0.139 mmol) in 1 ml of hexanes. The resulting mixture was stirred for 16 hours and a yellow solution was formed. The yellow solution was filtered from the traces of a gray solid (~1–2 mg). Hexanes and an excess of trimethylaluminum were removed under vacuum. Triphenylethane $Ph_3CCH_3$ was removed from the reaction products by sublimation at 55° C. for 1 h under vacuum ($10^{-4}$ torr), leaving a yellow-brown sticky solid (very thick oil). Yield of $Al(CH_3)_2(1\text{-}C_{12}H_{25}\text{---}CB_{11}F_{11})$ was approximately 0.021 g (93%). The solubility of $Al(CH_3)_2(1\text{-}C_{12}H_{25}\text{---}CB_{11}F_{11})$ in hexanes was at least 0.02 M, and the solubility of $Al(CH_3)_2(1\text{-}C_{12}H_{25}\text{---}CB_{11}F_{11})$ in methylcyclohexane was at least 0.05 M.

$^{19}F$ NMR (toluene-$d_8$): $\delta$–236.9 (1 F), –249.6 (5 F), –250.6 (5 F);

$^1H$ NMR (toluene-$d_8$): $\delta$2.43 (2 H), 1.89 (2 H), 1.28 (10 H), 1.16 (6 H), 1.05 (2 H), 0.93 (3 H), –0.73 (~6 H).

$^{19}F$ NMR (methylcyclohexane-$d_{14}$): $\delta$–240.9 (1 F), –246.0 (5 F), –248.3 (5 F);

$^1H$ NMR (methylcyclohexane-$d_{14}$): $\delta$2.27 (2 H), 1.78 (2 H), 1.30 (18 H), 0.89 (3 H), –0.21 (4 H), –0.42 (2 H).

Experiment 4

This example illustrates a method for producing $Al(C_2H_5)_2(1\text{-}CH_3\text{---}CB_{11}F_{11})$.

A mixture of $[CPh_3][1\text{-}CH_3\text{---}CB_{11}F_{11}]$ (7.0 mg) and toluene-$d_8$ (0.4 ml) was treated with a solution of triethylaluminum $Al(C_2H_5)_3$ (10 mg) in 0.5 ml of toluene-$d_8$. During the following 6 days a red oil ($[CPh_3][1\text{-}CH_3\text{---}CB_{11}F_{11}]$) was disappeared and a clear colorless solution was formed. Proton NMR spectrum of the solution indicated that triphenylmethane $CPh_3H$ and ethane $C_2H_4$ formed, which is consistent with the formation of $Al(C_2H_5)_2(1\text{-}CH_3\text{---}CB_{11}F_{11})$ ($\delta^{19}F$–239.8 (1 F), –251.4 (5 F) and –251.7 (5 F)) according to the reaction:

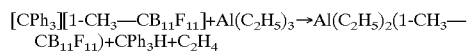

Experiment 5

This example illustrates a catalytic activity of $Al(CH_3)_2(1\text{-}CH_3\text{---}CB_{11}F_{11})$ for arene-olefin coupling.

A compound $Al(CH_3)_2(1\text{-}CH_3\text{---}CB_{11}F_{11})$ (2 mg) was dissolved in 1 ml of toluene-$d_8$ and transferred into a sealable NMR tube. The solution was degassed under vacuum and treated with 656 torr of ethylene for 14.5 hours at 24° C. Proton NMR spectrum of the solution indicated the formation of ethyltoluene. According to the integration of $^1H$ NMR signals, the molar amount of ethyltoluene produced was approximately 66 times larger than the molar amount of $Al(CH_3)_2(1\text{-}CH_3\text{---}CB_{11}F_{11})$ present in the solution. This fact indicated that the formation of ethyltoluene was catalytic (TON~66). A GC-MS analysis of the reaction mixture indicated the presence of all three positional isomers (i.e., the ortho (47%), meta (35%), and para (18%) isomers) of ethyltoluene $C_6D_4(CD_3)(CH_2CH_2D)$.

Experiment 6

This example illustrates a method for producing $Al(CH_3)_2((CH_3)_3NB_{12}F_{11})$.

A mixture of $[CPh_3][(CH_3)3NB_{12}F_{11}]$ (29 mg, 45 μmol) and toluene-$d_8$ (1.0 ml) was treated with a solution of trimethylaluminum $Al(CH_3)_3$ (11.0 mg, 150 μmol) in 0.5 ml of toluene-$d_8$. A mixture was stirred under a nitrogen atmosphere for 20 h. Proton NMR spectrum of the mixture indicated the formation of triphenylethane $CPh_3CH_3$. A light yellow solid was then separated from a clear colorless solution by filtration under a nitrogen atmosphere. The solid was washed 3 times with 1 ml of hexanes and dried under vacuum to provide approximately 14 mg (68% yield) of $Al(CH_3)_2((CH_3)_3NB_{12}F_{11})$. The compound was not soluble in toluene, but it was completely dissolved in acetonitrile-$d_3$ with formation of a clear colorless solution.

$^{19}$F NMR (acetonitrile-$d_3$): δ–259.3 (1 F), –262.9 (10 F);

$^1$H NMR (acetonitrile-$d_3$): δ3.15 (9 H), –0.74, –0.82, and –0.99 (~6 H total).

Experiment 7

This example illustrates a catalytic activity of $Al(CH_3)_2$ $(1-C_{12}H_{25}—CB_{11}F_{11})$ for polymerization of ethylene.

A suspension of $[CPh_3][1-C_{12}H_{25}—CB_{11}F_{11}]$ (5.0 mg) in 0.5 ml of methylcyclohexane-$d_{14}$ was treated with 0.5 ml of methylcyclohexane-$d_{14}$ solution of $Al(CH_3)_3$ (2.2 mg) for 20 h. The solution was filtered from the traces of a gray solid. The filtrate was diluted with 7 ml of hexanes and transferred into a 50 ml Kontes tube. The solution was treated with 703 torr of ethylene for 18 h at 24° C. and small amount of white solid was formed. The mixture was treated with 3 ml of methanol for 20 minutes. A solid polyethylene was collected (3 mg) by filtration and characterized by DSC ($T_m$=126° C.). The activity of $Al(CH_3)_2(1-C_{12}H_{25}—CB_{11}F_{11})$ for polymerization of ethylene in hexanes solution at 24° C. was calculated to be approximately 33 g PE/mol Al·h·at.

Experiment 8

This example illustrates that catalytic activity of $Al(CH_3)_2$ $(1-C_{12}H_{25}—CB_{11}F_{11})$ for polymerization of ethylene can be significantly increased by the addition of one equivalent of bis(cyclopentadienyl)dimethylzirconium $Cp_2ZrMe_2$.

A suspension of $[CPh_3][1-C_{12}H_{25}—CB_{11}F_{11}]$ (5.0 mg) in 0.5 ml of methylcyclohexane-$d_{14}$ was treated with 0.5 ml of methylcyclohexane-$d_{14}$ solution of $Al(CH_3)_3$ (2.2 mg) for 20 h. The solution was filtered from the traces of a gray solid. The filtrate was diluted with 7 ml of hexanes and transferred into a 50 ml Kontes tube. The solution was treated with 1 ml of hexanes solution of $Cp_2ZrMe_2$ (1.3 mg). The mixture was treated with 660 torr of ethylene. The ethylene pressure was decreased to 470 torr within 5 minutes due to the formation of polyethylene (white solid). More ethylene (812 torr) was added to the mixture and the ethylene pressure was decreased to 295 torr within the next 2 hours. The mixture was quenched with 5 ml of methanol and stirred for 20 minutes. A solid polyethylene was collected (210 mg) by filtration and characterized by DSC ($T_m$=129° C.). The catalytic activity during the first 5 minutes (good agitation) was calculated based on the ethylene pressure decrease and was at least 150 kg PE/mol Zr·h·atm.

Example 9

This example illustrates a catalytic activity of $Al(CH_3)_2$ $(1-CH_3—CB_{11}F_{11})$ for the alkylation of benzene with 1-hexene.

A mixture of $Al(CH_3)_2(1-CH_3—CB_{11}F_{11})$ (2.5 mg, 4.4 μmol), benzene (0.964 g, 12.4 mmol) and 1-hexene (0.224 g, 2.7 mmol) was stirred for 25 hours under a nitrogen atmosphere. A proton NMR spectrum of the reaction mixture indicated that no signals of 1-hexene were present in the reaction mixture after 25 hours. A GC-MS analysis of the reaction mixture indicated the formation of monohexylbenzenes (29%), dihexylbenzenes (20%) and trihexylbenzenes (51%). The relative amounts of 2-phenylhexane and 3-phenylhexane were 70% and 30%, respectively. Total turnovers number of aluminum alkyl catalyst was calculated to be approximately 606 (24 TON/h).

It has also been found that $Al(CH_3)_2(1-C_{12}H_{25}—CB_{11}F_{11})$ is an effective co-catalyst for the zirconocene catalyzed selective dimerization of 1-hexene (see Example 10 below). The advantages of Compounds of Formula I of the present invention toward the conventional co-catalyst (e.g., MAO) for the similar transformation include the absence of inductive period, higher total turnovers number of the catalyst (e.g., 4780 turn over number (TON) compare 500), and higher activity (315 TON·min$^{-1}$ compare to 30 TON·min$^{-1}$).

Example 10

This example illustrates that $Al(CH_3)_2(1-C_{12}H_{25}—CB_{11}F_{11})$ is an effective co-catalyst for the zirconocene catalyzed selective dimerization of 1-hexene.

A solution of $Al(CH_3)_2(1-C_2H_{25}—CB_{11}F_{11})$ (6.1 mg, 10.8 μmol) in 0.28 ml of methylcyclohexane was treated with a solution of $Cp_2ZrMe_2$ (2.3 mg, 9.1 μmol) in 1-hexene (3.654 g). The resulted mixture was stirred under a nitrogen atmosphere and the samples were taken from the reaction mixture after 5 minutes and 55 minutes. According to $^1$H NMR spectra of the reaction mixtures approximately 33% of 1-hexene were reacted within 5 minutes, and approximately 99% of 1-hexene were reacted within 55 minutes. The reaction was exothermic as indicated by the significant self-heating of the reaction mixture during the reaction. The reaction products were analyzed by $^1$H, $^{13}$C NMR and GC-MS. According to the analysis the reaction mixture contained 83% of 1-hexene dimerization products (more than 95% of 2-butyl-1-octene) and 17% of 1-hexene isomerization products (the distribution of hexene isomers was as follows: E-2 hexene—56%, Z-2 hexene—26%, E-3 hexene—15%, and Z-3 hexene—3%). The total turnovers number of the activated zirconocene catalyst was calculated to be 4780 (87 TON·min$^{-1}$). The turnovers number within the first five minutes of the reaction was approximately 315 TON·min$^{-1}$

Example 11

This example illustrates a method for producing $K_2B_{12}F_{12}$.

A 300 mL Monel reactor was charged with $K_2B_{12}H_{12}$ (0.82 g, 3.73 mmol) and hydrogen fluoride was added at –78° C. The reactor was rotated for 14 hours at 25° C., warmed up to 70° C. within two hours, and kept at this temperature for 5 hours. The reaction mixture was cooled down to –78° C., degassed and treated with 45 psi of 20% $F_2/N_2$ mixture. The reactor was rotated for 6 hours at 25° C. The reaction mixture was cooled down to –78° C., degassed and treated with 45 psi of 20% $F_2/N_2$ mixture. The reactor was rotated for 16 hours at 25° C. and the reaction mixture was treated with 45 psi of 20% $F_2/N_2$ mixture as described above. The reactor was rotated for 6 hours at 25° C. and the reaction mixture was treated with 45 psi of 20% $F_2/N_2$ mixture as described above. The reactor was rotated for 16 hours at 25° C., cooled down to –78° C. and the reaction mixture was degassed. Hydrogen fluoride was distilled out under vacuum and the solid reaction products were dissolved in 50 ml of water. The solution was neutralized with a solution of 0.9 g of KOH in 10 ml of water. A blue-green precipitate that formed was removed by filtration and the filtrate (pH~13–14) was neutralized with $H_2SO_4$ to pH=7. Water was removed from the solution under vacuum and the resulted solid was treated with 50 ml of acetonitrile. The insoluble material was removed by filtration and acetonitrile was removed under vacuum. The resulted white solid was dried under vacuum at 175° C. for 18 hours to provide 0.91 g of $K_2B_{12}F_{12}$ (Yield=56%).

Example 12

This example illustrates a method for producing $(CPh_3)_2B_{12}F_{12}$.

The compound $K_2B_{12}F_{12}$ (0.690 g, 1.584 mmol) was dissolved in 15 ml of acetonitrile and small amount of white insoluble material was removed by filtration. The filtrate was treated with a solution of $AgBF_4$ (0.617 g, 3.167 mmol) in 5 ml of acetonitrile for two hours. A white precipitate that formed was removed by filtration, dried under vacuum and 0.390 g of $KBF_4$ were collected (98% yield). The filtrate was treated with a suspension of $CPh_3Cl$ (0.882 g, 3.167 mmol) in 5 ml of acetonitrile for 16 hours. A white solid that formed was removed by filtration, dried under vacuum and 0.385 g of AgCl were collected (85% yield). The filtrate was concentrated down to 10 ml and approximately 40 mg of AgCl were collected (9% yield). Acetonitrile was removed from the filtrate under vacuum. The resulted orange solid was washed with 3×3 ml of dichloromethane, then with 1 ml of hexanes and dried under vacuum to provide 1.229 g of $(CPh_3)_2B_{12}F_{12}$ (Yield=92%).

$^1H$ NMR (acetonitrile-$d_3$): δ7.72 (6 H), 7.88 (6 H), 8.27 (3 H)

$^{19}F$ NMR (acetonitrile-$d_3$): δ−269.2 (12 F)

Example 13

This example illustrates a method for producing $((C_{18}H_{37})Me_2Si)_2B_{12}F_{12}$.

The compound $(CPh_3)_2B_{12}F_{12}$ (0.067 g, 0.079 mmol) was treated with an excess of $(n-C_{18}H_{37})Me_2SiH$ (0.8 ml) for one hour at 25° C. and then for one hour at 70° C. By that time the orange solid $(CPh_3)_2B_{12}F_{12}$ became a light yellow solid. Hexanes (1 ml) was added to the reaction mixture and the solid was collected by filtration. The solid was washed with 3×1 ml of hexanes and dried under vacuum to provide 0.070 g of white $((n-C_{18}H_{37})Me_2Si)_2B_{12}F_{12}$ (Yield=90%).

$^1H$ NMR (benzene-$d_6$): δ0.17 (6 H), 0.50 (2 H), 0.93 (3 H), 1.04 (2 H), 1.16 (2 H), 1.31 and 1.39 (28 H)

$^{19}F$ NMR (benzene-$d_6$): δ−260.1 (12 F)

$^1H$ NMR (acetonitrile-$d_3$): δ0.55 (6 H), 0.88 (3 H), 1.00 (2 H), 1.27 (32 H)

$^{19}F$ NMR (acetonitrile-$d_3$): δ−269.2 (12 F)

Example 14

This example illustrates a method for producing $[(n-C_{12}H_{25})_3NH]_2[B_{12}F_{12}]$.

The compound $[(n-Bu)_4N]_2[B_{12}F_{12}]$ (0.150 g, 0.178 mmol) was dissolved in 50 ml of methanol/acetonitrile 3/1 mixture and eluted through a column packed with Amberlist-15 cation exchange resin in its acidic form. Solvents were removed from elute under vacuum and the oily residue was dissolved in 30 ml of water. A viscous liquid $(n-C_{12}H_{25})_3N$ was added to the solution and the mixture was stirred until the viscous liquid disappeared and a white solid was formed (approximately 3 hours). Water was decanted out, the solid was washed with hexanes, collected by filtration and dried under vacuum at 150° C. for 18 h to provide 0.195 g of $[(n-C_{12}H_{25})_3NH]_2[B_{12}F_{12}]$ (Yield=78%).

$^1H$ NMR (toluene-$d_8$): δ0.97 (9 H), 1.36 (54 H), 1.50 (6 H), 2.82 (6 H), 6.02 (1 H)

$^{19}F$ NMR (toluene-$d_8$): δ−266.9 (12 F)

Example 15

This example illustrates a method for producing $(AlMe_2)_2B_{12}F_{12}$.

The orange microcrystalline compound $(CPh_3)_2B_{12}F_{12}$ (0.195 g, 0.231 mmol) was treated with 2 ml of toluene solution of $AlMe_3$ (0.161 g, 2.240 mmol). Approximately after 5–10 minutes of stirring a red-brown sticky soft solid and a yellow solution were formed. Approximately after 5–6 hours of stirring the red-brown sticky solid was disappeared and an amorphous yellow solid was formed. The mixture was stirred for additional 40 hours. The solid was removed by filtration, washed with 1 ml of toluene, then with 3×2 ml of hexanes and dried under nitrogen to provide 0.106 g of $(AlMe_2)_2B_{12}F_{12}$ (Yield=97%). The compound was not soluble in toluene but it was dissolved in acetonitrile-$d_3$ with the formation of a colorless solution.

$^1H$ NMR (acetonitrile-$d_3$): δ−0.75 and −0.99

$^{19}F$ NMR (acetonitrile-$d_3$): δ−268.7 (12 F)

Example 16

This example illustrates a process for synthesizing $Si(i-Pr)_3(1\text{-}Et\text{-}CB_{11}F_{11})$.

A suspension of $CPh_3(1\text{-}Et\text{-}CB_{11}F_{11})$ (0.412 g, 0.67 mmol) in pentane (40 ml) was treated with a solution of $Si(i-Pr)_3H$ (0.215 g, 1.36 mmol, 2 equiv.) in pentane (10 ml) for 20 hours at room temperature. The mixture was treated with more $Si(i-Pr)_3H$ (0.56 g, 3.54 mmol) for another 20 hours. (Note, that a large excess of $Si(i-Pr)_3H$ (~7 equiv.) required for the reaction to go to completion. A slightly pink pentane solution was filtered from a small amount of red-brown oily solid (~20 mg, which upon dissolving of in acetonitile was identified as a mixture of $CPh_3(1\text{-}Et\text{-}CB_{11}F_{11})$ and $[Si(i-Pr)_3(CD_3CN)][1\text{-}Et\text{-}CB_{11}F_{11}]$. The volume of the pentane solution was reduced to ~5 ml, which caused the formation of white solid. The solid was separated by filtration, washed three times with 1 ml of pentane and dried under nitrogen atmosphere inside the glove box. The yield of $Si(i-Pr)_3(1\text{-}Et\text{-}CB_{11}F_{11})$ as an off-white crystalline solid was 0.198 g (56%). The compound is extremely sensitive to the traces of water. The color of the solid changed from white to yellow-orange even during storage under nitrogen atmosphere inside the glove box.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

REFERENCES

1. Bochmann, M.; Sarsfield, M. J. *Organometallics*. 1998, 17, 5908.
2. Aeilts, S. L.; Coles, M. P.; Swenson, D. C.; Jordan, R. F. *Organometallics*. 1998, 17, 3265.
3. Coles, M. P.; Jordan, R. F. *J. Am. Chem. Soc.* 1997, 119, 8125.
4. Ihara, E.; Young, V. G.; Jordan, R. F. *J. Am. Chem. Soc.* 1998, 120, 8277.
5. Bruce, M.; Gibson, V. C.; Redshaw, C.; Solan, G. A.; White, A. J. P.; Williams, D. J. *Chem. Comm.* 1998, 2523.
6. Dohmeier, C.; Schnockel, Robl, C, Schneider, Ahlrichs, R. *Angew. Chem. Int. Ed. Engl.* 1993, 32, 1655.

7. Hair, G. S; Cowley, A. H.; Jones, R. A.; McBurnett, B. G.; Voigt, A. *J. Am. Chem. Soc.* 1999, 121, 4922.
8. Jia, C.; Lu, W.; Kitamura, T.; Fujiwara, Y. *Organic Letters.* 1999, 1, 2097.
9. Shilov, A. E.; Shul'pin, G. B. *Chem. Rev.* 1997, 97, 2879.
10. Alul, H.; McEwan, G. *J. Org. Chem.* 1972, 37, 3323.
11. Chen, E. Y.; Marks, T. *J. Chem. Rev.* 2000, 100, 1391.

What is claimed is:

1. A compound of the formula:

$$M_xQ_y,$$

wherein
 each M is independently a cation, provided at least one M is a reactive cation selected from the group consisting of silver cation, aluminum cation, silylium cation, ammonium cation, protonated arene, and triaryl carbocation;
 Q is a fluorinated polyhedral borate moiety selected from the group consisting of a monoheteroborate and an aminoborate which comprises a polyhedral borane having an amino group covalently attached to a single boron atom, provided when Q is a monoheteroborate then M is an aluminum cation;
 x is an absolute value of the oxidation state of Q; and
 y is an absolute value of the oxidation state of M.

2. The compound of claim 1, wherein said aluminum cation is a moiety of the formula $(R^1R^2Al)^{+1}$, wherein each of $R^1$ and $R^2$ is independently selected from the group consisting of alkyl, cycloalkyl, aryl, aralkyl, cycloalkalkyl, alkenyl, and halide.

3. The compound of claim 1, wherein said silylium cation is a moiety of the formula $(R^3R^4R^5Si)^{+1}$, wherein each of $R^3$, $R^4$, and $R^5$ is independently selected from the group consisting of hydrogen, alkyl, aryl, aralkyl, cycloalkyl, and halide.

4. The compound of claim 1, wherein said ammonium cation is a moiety of the formula $(R^{16}R^{17}R^{18}NH)^{+1}$, wherein each of $R^{16}$, $R^{17}$, and $R^{18}$ is independently selected from the group consisting of hydrogen, alkyl, aryl, aralkyl, cycloalkyl, and silyl.

5. The compound of claim 4, wherein each of $R^{16}$, $R^{17}$, and $R^{18}$ is independently selected from the group consisting of alkyl, aryl, aralkyl, and cycloalkyl.

6. The compound of claim 1, wherein said monoheteroborate is of the formula $((R^6)_aZB_bH_cF_dX_e(OR^7)_f)^{-1}$, wherein $R^6$ is bonded to Z, Z is bonded to B, and each of H, F, X, and $OR^7$ is bonded to a different boron atom,
and wherein
 $R^6$ is selected from the group consisting of polymer, hydrogen, halide, alkyl, cycloalkyl, alkenyl, alkynyl, and aryl;
 Z is selected from the group consisting of C, Si, Ge, Sn, Pb, N, P, As, Sb, and Bi;
 each X is independently halide;
 $R^7$ is selected from the group consisting of polymer, hydrogen, alkyl, cycloalkyl, alkenyl, alkynyl, and aryl;
 a is 0 or 1;
 b is an integer from 5 to 13;
 c is an integer from 0 to 12;
 d is an integer from 2 to 13;
 e is an integer from 0 to 11;
 f is an integer from 0 to 5; and
 the sum of c+d+e+f is b.

7. The compound of claim 1, wherein said aminoborate is a moiety of the formula $(R^8R^9R^{10}NB_gH_hF_i)^{-1}$, wherein $R^8$, $R^9$, and $R^{10}$ are bonded to N, and N is bonded to boron, and each of H and F is bonded to a different boron atom,
and wherein
 each of $R^8$, $R^9$, and $R^{10}$ is independently selected from the group consisting of hydrogen, alkyl, cycloalkyl, aryl, aralkyl, and a polymer;
 g is an integer from 6 to 14;
 h is an integer from 0 to 13;
 i is an integer from 1 to 14; and
 the sum of 1+h+i is g.

8. The compound according to claim 1 of the formula $(R^1R^2Al)[(R^6)_aZB_bH_cF_dX_e(OR^7)_f]$, where $R^6$ is bonded to Z, Z is bonded to B, and each of H, F, X, and $OR^7$ is bonded to a different boron atom,
wherein
 each of $R^1$ and $R^2$ is independently selected from the group consisting of alkyl, cycloalkyl, aryl, aralkyl, cycloalkalkyl, alkenyl, and halide;
 $R^6$ is selected from the group consisting of polymer, hydrogen, halide, alkyl, cycloalkyl, alkenyl, alkynyl, and aryl;
 Z is selected from the group consisting of C, Si, Ge, Sn, Pb, N, P, As, Sb, and Bi;
 each X is independently halide;
 $R^7$ is selected from the group consisting of polymer, hydrogen, alkyl, cycloalkyl, alkenyl, alkynyl, and aryl;
 a is 0 or 1;
 b is an integer from 5 to 13;
 c is an integer from 0 to 12;
 d is an integer from 2 to 13;
 e is an integer from 0 to 11;
 f is an integer from 0 to 5; and
 the sum of c+d+e+f is b.

9. The compound according to claim 8, wherein Z is C and a is 1.

10. The compound according to claim 9, wherein $R^6$ is selected from the group consisting of alkyl, aryl, and silyl.

11. The compound according to claim 10, wherein c, e, and f are 0.

12. The compound according to claim 11, wherein b and d are 11.

13. The compound according to claim 12, wherein $R^6$ is selected from the group consisting of methyl, ethyl, dodecyl, butyl, iso-butyl, t-butyl, silyl, propyl, iso-propyl, pentyl, hexyl, and a polymer.

14. The compound according to claim 8, wherein each of $R^1$ and $R^2$ is independently selected from the group consisting of alkyl, aryl, and halide.

15. The compound according to claim 14, wherein $R^1$ and $R^2$ are methyl, ethyl, iso-propyl, propyl, butyl, iso-butyl, t-butyl, pentyl, hexyl, and halide.

16. The compound according to claim 1 of the formula $(R^1R^2Al)[R^8R^9R^{10}N-B_gH_hF_i]$, where $R^8$, $R^9$, and $R^{10}$ are bonded to N, and N is bonded to boron, and each of H and F is bonded to a different boron atom,
wherein
 each of $R^1$ and $R^2$ is independently selected from the group consisting of alkyl, cycloalkyl, aryl, aralkyl, cycloalkakyl, alkenyl, and halide;
 each of $R^8$, $R^9$, and $R^{10}$ is independently selected from the group consisting of hydrogen, alkyl, cycloalkyl, aryl, aralkyl, and a polymer;
 g is an integer from 6 to 14;

h is an integer from 0 to 13;

i is an integer from 1 to 14; and the sum of 1+h+i is g.

17. The compound according to claim 16, wherein g is 12, i is 11 and h is 0.

18. The compound according to claim 17, wherein $R^8$, $R^9$, and $R^{10}$ are alkyl.

19. The compound according to claim 18, wherein each of $R^8$, $R^9$, and $R^{10}$ is independently selected from the group consisting of methyl, ethyl, hexyl, octyl, and dodecyl.

20. The compound according to claim 19, wherein each of $R^1$ and $R^2$ is independently selected from the group consisting of alkyl, aryl, and halide.

21. The compound according to claim 20, wherein each of $R^1$ and $R^2$ is independently selected from the group consisting of methyl, ethyl, iso-propyl, propyl, butyl, iso-butyl, t-butyl, pentyl, hexyl, and halide.

22. A process for producing a fluorinated polyhedral borate compound of the formula $M_pQ_q$ comprising a reactive cation, said process comprising the steps of:
   (i) fluorinating a non-fluorinated compound of the formula $M^1_pQ^1_q$ by contacting said non-fluorinated compound with HF, $F_2$ or mixtures thereof under conditions sufficient to produce a fluorinated salt of the formula $M^1_pQ_q$,
   wherein
   each
   $M^1$ is a non-reactive cation;
   $Q^1$ is a nonfluorinated polyhedral borate moiety selected from the group consisting of a monoheteroborate, an aminoborate which comprises a polyhedral borate having an amino group covalently attached to a single boron action, and a polyhalogenated borate;
   Q is a fluorinated $Q^1$; and
   p is an absolute value of the oxidation state of $Q^1$;
   q is an absolute value of the oxidation state of $M^1$, and
   (ii) exchanging said non-reactive cation with a reactive cation to produce said fluorinated polyhedral borate compound of the formula $M_pQ_q$,
   wherein
   each M is independently a cation, provided at least one M is a reactive cation selected from the group consisting of silver cation, aluminum cation, silylium cation, ammonium cation, protonated arene, and triaryl carbocation,
   provided when $Q^1$ is a monoheteroborate then at least one of the M is an aluminum cation.

23. The process of claim 22, wherein said reactive cation is a triaryl carbocation.

24. The process of claim 23, wherein said cation exchange step comprises contacting said fluorinated salt of the formula $M^1_pQ_q$ with a triaryl carbocation boron tetrafluoride under conditions sufficient to exchange said non-reactive cation with said triaryl carbocation,
wherein
$M^1$, Q, p, and q are those defined in claim 22.

25. The process of claim 23, wherein said cation exchange step comprises the steps of:
   (a) contacting said fluorinated salt of the formula $M^1_pQ_q$ with silver boron tetrafluoride to produce a silver salt of the formula $(M^1)_mAg_nQ_q$, wherein
   $M^1$, Q, p, and q are those defined in claim 22;
   m is 0 or 1;
   n is 1 or 2, provided the sum of m+n is an absolute value of the oxidation state of Q; and (b) contacting said silver salt with a triaryl halide under conditions sufficient to exchange said silver cation with said triaryl carbocation.

26. The process of claim 22, wherein said reactive cation is silver cation.

27. The process of claim 26, wherein said cation exchange step comprises the steps of contacting said fluorinated salt of the formula $M^1_pQ_q$ with silver boron tetrafluoride under conditions sufficient to exchange said non-reactive cation with said silver cation,
wherein
$M^1$, Q, p, and q are those defined in claim 22.

28. The process of claim 22, wherein said reactive cation is selected from the group consisting of
   (a) silylium cation of the formula $(R^3R^4R^5Si)^{+1}$, wherein each of $R^3$, $R^4$, and $R^5$ is independently selected from the group consisting of hydrogen, alkyl, aryl, aralkyl, cycloalkyl, and halide; and
   (b) aluminum cation of the formula $(R^1R^2Al)^{+1}$, wherein each of $R^1$ and $R^2$ is independently selected from the group consisting of alkyl, cycloalkyl, aryl, aralkyl, cycloalkalkyl, alkenyl, and halide.

29. The process of claim 28, wherein said cation exchange step further comprises the steps of:
   (a) converting said fluorinated salt of the formula $M^1_pQ_q$ to a fluorinated salt comprising a triaryl carbocation; and
   (b) contacting said triaryl carbocation comprising fluorinated salt with a compound of the formula $R^3R^4R^5SiH$ or $R^1R^2AlR^{19}$ under conditions sufficient to produce a fluorinated compound of the formula $(M^1)_m(R^3R^4R^5Si)_nQ_q$ or $(M^1)_m(R^1R^2Al)_nQ_q$, respectively,
   wherein
   $R^{19}$ is selected from the group consisting of hydrogen and alkyl;
   m is 0 or 1;
   n is 1 or 2, provided the sum of m+n is an absolute value of the oxidation state of Q;
   $M^1$, Q, p and q are those defined in claim 22, and
   $R^1$, $R^2$, $R^3$, $R^4$, and $R^5$ are those defined in claim 28.

30. The process of claim 22, wherein said reactive cation is an ammonium cation of the formula $(R^{16}R^{17}R^{18}NH)^{+1}$, wherein each of $R^{16}$, $R^{17}$, and $R^{18}$ is independently selected from the group consisting of hydrogen, alkyl, aryl, aralkyl, cycloalkyl, and silyl.

31. The process of claim 30, wherein said cation exchange step farther comprises the steps:
   (a) acidifying said fluorinated salt of the formula $M^1_pQ_q$ under conditions sufficient to produce an acidic fluorinate salt of the formula $(M^1)_mH_nQ_q$; and
   (b) contacting said acidic fluorinated salt with an amine of the formula $R^{16}R^{17}R^{18}N$ to produce an ammonium fluorinated borate salt of the formula $(M^1)_m(R^{16}R^{17}R^{18}NH)_nQ$,
   wherein
   $R^{16}$, $R^{17}$, and $R^{18}$ are those defined in claim 30,
   m is 0 or 1;
   n is 1 or 2, provided the sum of m+n is an absolute value of the oxidation state of Q; and
   $M^1$, Q, p and q are those defined in claim 22.

32. The process of claim 22, wherein said reactive cation is a protonated arene of the formula $(Ar^1H)^{+1}$, wherein $Ar^1$ is an optionally substituted aryl.

* * * * *

UNITED STATES PATENT AND TRADEMARK OFFICE
CERTIFICATE OF CORRECTION

PATENT NO.    : 6,448,447 B1
DATED         : September 10, 2002
INVENTOR(S)   : Steven H. Stauss and Sergei V. Ivanov It is certified that error appears in the above-identified patent and that said Letters Patent is hereby corrected as shown below:

<u>Column 1,</u>
Line 16, please add:
-- STATEMENT REGARDING FEDERALLY SPONSORED RESEARCH
    The U.S. Government has a paid-up license in this invention and the right in limited circumstances to require the patent owner to license others on reasonable terms as provided for by the terms of Grant No. CHE-9905482 awarded by the National Science Foundation. --

Signed and Sealed this

Fourth Day of February, 2003

JAMES E. ROGAN
*Director of the United States Patent and Trademark Office*